US006242416B1

(12) United States Patent
Gilchrest et al.

(10) Patent No.: US 6,242,416 B1
(45) Date of Patent: Jun. 5, 2001

(54) INHIBITION OF β-AMYLOID BINDING TO THE P75 NERVE GROWTH FACTOR RECEPTOR

(75) Inventors: Barbara A. Gilchrest, Boston; Mina Yaar, Sharon, both of MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/163,095

(22) Filed: Sep. 29, 1998

Related U.S. Application Data (63) Continuation-in-part of application No. PCT/US97/04966, filed on Mar. 28, 1997, which is a continuation-in-part of application No. 08/625,765, filed on Mar. 29, 1996, now abandoned.

(51) Int. Cl.[7] .......................... A61K 38/00; A01N 37/18
(52) U.S. Cl. .................. 514/2; 514/14; 514/15; 514/16; 514/17; 514/18
(58) Field of Search .................. 514/2, 15, 14, 514/16, 17, 18; 530/399

(56) References Cited

U.S. PATENT DOCUMENTS

| 5,288,641 | 2/1994 | Roizman . |
| 5,576,209 | 11/1996 | Bredesen . |

FOREIGN PATENT DOCUMENTS

| 0 584 452 A1 | 3/1994 | (EP) . |
| 92/18149 | 10/1992 | (WO) . |
| 95/21193 | 8/1995 | (WO) . |
| 96/10182 | 4/1996 | (WO) . |
| 96/12955 | 5/1996 | (WO) . |
| WO97/37228 | 10/1997 | (WO) . |

OTHER PUBLICATIONS

Park, H–Y., et al., "The β Isoform of Protein Kinase C Stimulates Human Melanogenesis by Activating Tyrosinase in Pigment Cells," *J. Biol. Chem.*, 268(16):11742–11749 (1993).

Veis, D.J., et al., "Bcl–2–Deficient Mice Demonstrate Fulminant Lymphoid Apoptosis, Polycystic Kidneys, and Hypopigmented Hair," *Cell*, 75:229–240 (1993).

Furuya, H., et al., "Amyloid β–Protein Gene Duplication is Not Common in Alzheimer's Disease: Analysis by Polymorphic Restriction Fragments," *Biochem. and Biophys Research Comm.*, 150 (1):75–81 (1988).

Ikeda, S–I, et al., "Immunoglob Labeling of Cerebrovascular and Neuritic Plaque Amyloid Fibrils in Alzheimer's Disease with an Anti–β Protein Monoclonal Antibody," *Lab. Inv.*, 57(4):446–449 (1987).

Sasaki, H., et al., "A HindIII Polymorphism Detected by the cDNA Encoding Amyloid Beta Protein of Alzheimer's Disease," *Nucleic–Acids Research.*, 15(15):6309 (1987).

Selkoe, D.J., "Normal and Abnormal Biology of the β–Amyloid Precursor Protein," *Annu. Rev. Neurosci.*, 17:489–517 (1994).

Lu, B., et al., "A Model for Keratinocyte Gene Therapy: Preclinical and Therapeutic Considerations," *Proc. Assoc Amer. Physic.*, 108(2):165–172 (1996).

Selkoe, D.J., "Amyloid Protein and Alzheimer's Disease," *Scientific Amer.*, 68–78 (1991).

Zhai, S., et al., "Nerve Growth Factor (NGF) Enhances Survival of Human Melanocytes," *J. Invest. Dermat.*, 101, Abstract No. 279, p. 434 (1993).

Zhai, S., et al., "A Role for P57 Nerve Growth Factor Receptor in Programmed Melanocyte Cell Death After Injury and With Aging," *J. Invest. Dermat.*, 102(4):545 (Abstract No. 131), (1994).

Hempstead, B.L., et al., "High–Affinity NGF Binding Requires Coexpression of the trk Proto–Oncogene and the Low–Affinity NGF Receptor," *Nature*, 350:678–682 (1991).

Ross, A., et al., "Characterization of Nerve Growth Factor Receptor in Neural Crest Tumors Using Monoclonal Antibodies," *Proc. Natl. Acad. Sci.*, 81:6681–6685 (1984).

Rabizadeh, S., et al., "Induction of Apoptosis by the Low–Affinity NGF Receptor," *Science*, 261:345–348 (1993).

Levy–Lahad, E., et al., "A Familial Alzheimer's Disease Locus on Chromosome 1," *Science*, 269:970–972 (1995).

Rabizadeh, S., et al., "Expression of the Low–Affinity Nerve Growth Factor Receptor Enhances β–Amyloid Peptide Toxicity," *Proc. Natl. Acad. Sci. USA*, 91:10703–10706 (1994).

Geller, A.I. and Breakefield, Y.O., "A Defective HSV–1 Vector Expresses *Escherichia coli* β–Galactosidase in Cultured Peripheral Neurons," *Science* 241:1667–1669 (1988).

Su, J.H., et al., "Immunohistochemical Evidence for Apoptosis in Alzheimer's Disease," *Neuroreport.*, 5(18):2529–2533 (1994).

(List continued on next page.)

Primary Examiner—Patricia A. Duffy
(74) Attorney, Agent, or Firm—Hamilton, Brook, Smith & Reynolds, P.C.

(57) ABSTRACT

Methods of inhibiting β-amyloid-mediated activation of the p75 nerve growth factor receptor of a cell that expresses the p75 nerve growth factor receptor are provided. Methods of inhibiting the binding of β-amyloid protein and β-amyloid peptides to the p75 nerve growth factor receptor, and methods of inhibiting β-amyloid-mediated apoptosis of neural crest-derived cells are provided. The methods comprise contacting the cell with a substance, comprising, for example, the amino acid sequence lysine-glycine-lysine (KGK) or lysine-glycine-alanine (KGA), wherein the substance binds to the p75 nerve growth factor receptor, resulting in the inhibition of β-amyloid protein or β-amyloid peptide binding to and/or activation of the p75 nerve growth factor receptor, or wherein the substance inhibits β-amyloid protein or β-amyloid peptide mediated apoptosis of the cell which expresses the p75 nerve growth factor receptor.

10 Claims, 3 Drawing Sheets

OTHER PUBLICATIONS

Nordberg, A., "Clinical Studies in Alzheimer Patients With Positron Emission Tomography," *Behav. Brain Research,* 57:215–224 (1993).

Seiger, A., et al., "Intracranial Infusion of Purified Nerve Growth Factor to an Alzheimer Patient: The First Attempt of a Possible Future Treatment Strategy," *Behav. Brain Res.,* 57:255–261 (1993).

Reiman, E.M., et al., "Preclinical Evidence of Alzheimer's Disease in Persons Homozygous for the ∈4 Allele for Apolipoprotein E," *N.E. J. Medicine,* 334(12):752–758 (1996).

Ibáñez, C.F., et al., "Disruption of the Low Affinity Receptor–Binding Site in NGF Allows Neuronal Survival and Differentiation by Binding to the trk Gene Product," *Cell,* 69:239–341 (1992).

Garcia, I., et al., "Prevention of Programmed Cell Death of Sympathetic Neurons by the bcl–2 Proto–Oncogene," *Science,* 258:302–304 (1992).

Dobrowsky, R.T., et al., "Activation of the Sphingomyelin Cycle Through the Low–Affinity Neurotrophin Receptor," *Science,* 265:1596–1599 (1994).

Yamazaki, T., et al., "Trafficking of Cell Surface β–Amyloid Precursor Protein: Retrograde and Transcytotic Transport in Cultured Neurons," *J. Cell Biol.,* 129(2):431–442 (1995).

Oltavi, Z.N., et al., "Bcl–2 Heterodimerizes In Vivo with a Conserved Homolog, Bax, That Accelerates Programmed Cell Death," *Cell,* 74:609–619 (1993).

Allsopp, T.E., et al., "The Proto–Oncogene bcl–2 Can Selectively Rescue Neurotrophic Factor–Dependent Neurons from Apoptosis," *Cell,* 73:295–307 (1993).

Levy–Lahad, E., et al., ,"Candidate Gene for the Chromosome 1 Familial Alzheimer's Disease Locus," *Science,* 269:293–977 (1995).

Boland, K., et al., "Specificity in Recognition of Amyloid–β Peptide by the Serpin–Enzyme Complex Receptor in Hepatoma Cells and Neuronal Cells," *J. Biol. Chem,* 270(47):28022–28028 (1995).

Barinaga, M., "Missing Alzheimer's Gene Found," *Science,* 269:917–918 (1995).

Yaar, M., et al., "Evidence for Nerve Growth Factor–Mediated Paracrine Effects in Human Epidermis," *J. Cell Biol.,* 115(3):821–828 (1991).

Ulrich, A., et al., "Human β–Nerve Growth Factor Gene Sequence Highly Homologous to that of Mouse," *Nature,* 303:821–825 (1983).

Peacocke, M., et al., "Induction of Nerve Growth Factor Receptors on Cultured Human Melanocytes," *Proc. Natl. Acad. Sci. USA,* 85:5282–5286 (1988).

Selkoe, D.J., "The Molecular Pathology of Alzheimer's Disease," *Neuron,* 6:487–498 (1991).

Battleman, D.S., "HSV–1 Vector–Mediated Gene Transfer of the Human Nerve Growth Factor Receptor p75$^{hNGFR}$ Defines High–Affinity NGF Binding," *J. Neuroscience,* 13(3):941–951 (1993).

Anderson, W., et al., "Amyloid Precursor Protein and Secreted β Amyloid Peptides: Novel Autocrine Factors Affecting Melanocytes," *J. Invest. Dermatol.* 104(4):585 (Abstract No.: 182) (1995).

Lapchak, P.A., "Nerve Growth Factor Pharmacology: Application to the Treatment of Cholinergic Neurodegeneration in Alzheimer's Disease," *Exp. Neurology,* 124:16–20 (1993).

Halaban, R., et al., "Growth Factors, Receptor Kinases, and Protein Tyrosine Phosphatases in Normal and Malignant Melanocytes," *J. Immunotherapy,* 12:154–161 (1993).

Verdi, J.M., et al., "Expression of trk in MAH cells lacking the p75 Low–Affinity Nerve Growth Factor Receptor is Sufficient to Permit Nerve Growth Factor–Inducted Differentiation to Postmitotic Neurons," *Proc. Natl. Acad. Sci. USA,* 91:3949–3953 (1994).

Zhai, S., et al., "Nerve Growth Factor Rescues Pigment Cells From Ultraviolet–Induced Apoptosis by Upregulating BCL–2 Levels," *Exper. Cell Res.,* 224:335–343 (1996).

Lavy–Lahad, E., et al., "Candidate Gene for the Chromosome 1 Familial Alzheimer's Disease Locus," *Science,* 269:973–977 (1995).

Cotman, C.W. and Anderson, A.J., "A Potential Role for Apoptosis in Neurodegeneration and Alzheimer's Disease," *Mol. Neurobio.,* 10:19–49 (1995).

Mark A.J., et al., "Amyloid β–Peptide Impairs Ion–Motive ATPase Activates: Evidence for a Role in Loss of Neuronal $Ca^{2+}$ Homeostasis and Cell Death," *J. Neuroscience,* 15(9):6239–6249 (1995).

Olson, L., et al., "Nerve Growth Factor Affects $^{11}$C–Nicotine Binding, Blood Flow, EEG, and Verbal Episodic Memory in an Alzheimer Patient (case report)," *J. Neural Trans.,* 4(1):79–95 (1992).

Lapchak, P.A., "Nerve Growth Factor Pharmacology: Application to the Treatment of Cholinergic Neurodengeneration in Alzheimer's Disease," *Experimental Neurology,* 124:16–20 (1993).

Yaar, M., et al., "Binding of β–Amyloid to the p75 Neurotrophin Receptor Induces Apoptosis, a Possible Mechanism for Alzheimer's Disease," *The Journal of Clincal Investigation,* 100(9):2333–2340 (Nov. 1997).

Yanker, B.A., et al., "Nerve Growth Factor Potentiates the Neurotoxicity of β Amyloid," *Proc. Natl., Acad. Sci. USA,* 87:9020–9023 (1990).

Yaar, M. and Gilchrest, B.A., "Human Melanocytes as a Model System for Studies of Alzheimer Disease," *Arch Dermatol.,* 133:1287–1291 (1997).

Van Der Zee, C.E.E.M., et al., "Survival of Cholinergic Forebrain Neurons in Developing p75$^{NGFR}$–Deficient Mice," *Science,* 274:1729–1732 (1996).

INHIBITION OF β-AMYLOID BINDING TO THE P75 NERVE GROWTH FACTOR RECEPTOR

RELATED APPLICATIONS

This application is a continuation-in-part of PCT/US97/04966, filed Mar. 28, 1997, which is a continuation-in-part of prior Ser. No. 08/625,765 filed Mar. 29, 1996 now abandoned, the entire teachings of which are incorporated herein by reference.

BACKGROUND OF THE INVENTION

Dementia is a condition of deteriorating mentality that is characterized by marked decline in the individual's former intellectual level, including memory loss, impaired judgment, speech and orientation, and is often accompanied by emotional apathy. (WEBSTER'S MEDICAL DESK DICTIONARY, Merriam-Webster, Inc., Springfield, Mass. p.169 (1986)).

A leading cause of dementia is Alzheimer's disease,(AD), a neurodegenerative disorder affecting 17 to 20 million people worldwide (Yamazaki, T., et al., *J. Cell. Biol.*, 129;431–442 (1995); Brinaga, M., *Science*, 269:917–918 (1995); Lavy-Lahad, E., et al., *Science*, 269:970–972 (1995); Lavy-Lahad, E., et al., *Science*, 269:973–977 (1995)). AD is characterized by progressive dementia together with neuropathological findings of "isenile plaques" in the brain formed by deposits of β-amyloid protein, surrounded by clusters of degenerating neurons. β-amyloid protein itself is a fragment of the 770 amino acid membrane bound β-amyloid precursor protein (βAPP) that is expressed in both neuronal and non-neuronal tissues.

Muteins of βAPP have been produced for the purpose of developing a βAPP substrate system wherein βAPP is cleavable or not cleavable such that βAP producing enzymes and inhibitors thereof may be isolated.

The specific cause of Alzheimer's disease has not yet been determined. A mutation in the βAPP gene in families with one form of autosomal dominant AD was found to be associated with increased β-amyloid synthesis and aggregation in the brain. A receptor for βAPP has been identified as the low density lipoprotein receptor-related protein, ApoE, and it has been postulated that this receptor protein, the enzyme responsible for βAPP cleavage in the cell membrane, production of βAPP and/or production of extra-cellular matrix molecules may be abnormal individually or in combination in AD patients, resulting in excess β-amyloid deposition and the observed neurotoxicity. However, the mechanism by which other known βAPP gene mutations cause AD, as well as the pathophysiology of non-familial AD in which βAPP gene mutations have not been recognized, is not understood.

Therefore, diagnosing Alzheimer's disease as the cause of an individual's dementia, as well as treating AD and developing drug therapies is very difficult. Although recent reports of using Positron-emission tomography (PET) (Reiman, E. M., et al., *New Eng. J. Med.*, 334:752–758 (1996), determining the genotype of an individual's ApoE, or measuring the levels of β-amyloid protein in cerebral spinal fluid may be promising, diagnosis of Alzheimer's is currently confirmed only upon autopsy to determine the presence of β-amyloid senile plaques.

In vitro systems employed to study Alzheimer's disease to date consist of malignant, or transformed cells that are not of neural crest origin, or lower vertebrate neuronal cultures. It would be of great advantage to have an Alzheimer's disease model system using normal human neural crest-derived cells. However, to date, no such model system has been developed.

Moreover, recent studies have shown that damage to CNS neurons due to Alzheimer's disease begins years before clinical symptoms are evident. (Reiman, E. M., et al., *New Eng. J. Med.*, 334:752–758 (1996)), suggesting that therapy could begin in the pre-symptomatic phase of the disease if a sensitive diagnostic test and targeted therapies were available. There exists a great need to determine the physiological mechanisms involved with the disease and for an accurate and easy to perform assay to evaluate the risk of developing Alzheimer's disease.

SUMMARY OF THE INVENTION

The present invention relates to the discovery that neurons and epidermal melanocytes are neural crest-derived cells that undergo β-amyloid mediated apoptosis mediated by β-amyloid binding to the same receptor, the 75 kD neurotrophin receptor ($p75^{NTR}$). As used herein, the term β-amyloid protein is intended to encompass β-amyloid protein (a 4.2 kD polypeptide (Selkoe, D. J., *Neuron*, 6:487–498 (1991); Glenner G. G. and Wong, C. W., *Biochem. Biophys. Res. Commun.*, 120:885–890 (1993), the teachings of which are herein incorporated by reference), β-amyloid precursor protein (βAPP), and fragments of β-amyloid and β-amyloid precursor protein referred to herein as β-amyloid peptides, including β-amyloid 1–40 peptide, β-amyloid 1–42 peptide, β-amyloid 25–36 peptide or β-amyloid 28–30 peptide. (β-amyloid protein is also referred to herein as β-amyloid).

More specifically, it is demonstrated herein that β-amyloid protein or peptide binds to the p75 nerve growth factor receptor ($p75^{NTR}$) of neural crest-derived cells, e.g. melanocytes, resulting in apoptosis of the cell. It is further demonstrated herein that inhibiting the binding of β-amyloid protein or peptide to the p75 nerve growth factor receptor, results in inhibiting the activation of the p75 nerve growth factor receptor, which in turn inhibits apoptosis.

The present invention relates to-methods of inhibiting β-amyloid-mediated activation of the p75 nerve growth factor receptor of a cell that expresses the p75 nerve growth factor receptor, methods of inhibiting the binding of β-amyloid protein and β-amyloid peptides to the p75 nerve growth factor receptor, and methods of inhibiting β-amyloid-mediated apoptosis of neural crest-derived cells. The methods comprise contacting the cell with a substance, comprising, for example, the amino acid sequence lysine-glycine-lysine (KGK) or lysine-glycine-alanine (KGA), wherein the substance binds to the p75 nerve growth factor receptor, resulting in the inhibition of β-amyloid protein or β-amyloid peptide binding to and/or activation of the p75 nerve growth factor receptor, or wherein the substance inhibits β-amyloid protein or β-amyloid peptide mediated apoptosis of the cell which expresses the p75 nerve growth factor receptor.

It is has been reported that cell death receptors mediate apoptosis by aggregation resulting from ligand binding or membrane perturbation. Applicants have demonstrated that β-amyloid aggregates the $p75^{NTR}$ thereby inducing cell death. Peptides, specifically cyclic peptides, bind the receptors individually and block aggregation of the $p75^{NTR}$, thereby inhibiting apoptosis. Specifically encompassed by the present invention are cyclic peptides (e.g., peptides in a β-loop conformation) which comprise lysine-glycine-lysine or lysine-glycine-alanine, or other sequences capable of binding to the $p75^{NTR}$.

Activation of the p75 nerve growth factor receptor can be determined by measuring the β-amyloid activation of the p75 nerve growth factor receptor of neural crest-derived cells, in culture or in a tissue sample, in the presence of the test substance and comparing the results with the β-amyloid activation of the p75 nerve growth factor receptor of neural crest-derived cells in a control culture or sample without the test-substance. A decrease of β-amyloid activation of the p75 nerve growth factor receptor of neural crest-derived cells in the test sample compared to β-amyloid activation of the p75 nerve growth factor receptor of neural crest-derived cells in the control sample is indicative of a substance that inhibits β-amyloid-mediated apoptosis in neural crest-derived cells.

The present invention further relates to in vitro methods of screening substances and identifying those substances capable of inhibiting, or decreasing cell apoptosis mediated by β-amyloid, or activation of the $p75^{NTR}$, and to substances identified by these methods.

The method of identifying substances that inhibit β-amyloid-mediated apoptosis of cells that express the p75 nerve growth factor receptor comprises contacting the cells, in culture or in a tissue sample, with β-amyloid protein, or peptide and with the substance to be tested, wherein the β-amyloid protein/peptide is at a concentration sufficient to bind to and activate the p75 nerve growth factor receptor, thereby producing a test sample. The test sample is maintained under conditions sufficient for the β-amyloid protein or peptide or test-substance to bind to the p75 nerve growth factor receptor expressed on the cells and activation of the p75 nerve growth factor receptor is determined, thereby identifying substances that inhibit apoptosis.

The present invention further relates to methods of diagnosing and treating Alzheimer's disease, and other neurodegenerative diseases mediated by β-amyloid protein, or by aberrant activation of the low affinity nerve growth factor receptor localized on neural cell surfaces. For example, autoimmune encephalomyelitis, Huntington's disease, Pick's disease, corticobasal degeneration, progressive supranuclear palsy, Gerotman-Shausslesr Scheinker syndrome, Niemann-Pick disease, Down's Syndrome and progressive supranuclear palsy are encompassed by this invention.

Neurodegenerative diseases mediated by β-amyloid protein encompass diseases affecting neural crest-derived cells, such as central nervous system (CNS) neurons and in which β-amyloid protein, βAPP, or β-amyloid peptides initiate, or exacerbate, a process leading to neuron degeneration, or neuronal cell death. Neurodegenerative diseases mediated by aberrant activation of the low affinity nerve growth factor encompasses diseases in which the low affinity nerve growth factor is activated by a substance resulting in apoptotic cell death. The neurodegenerative diseases encompassed by the present invention are characterized by progressive dementia in the affected individual. Specifically encompassed by the present invention is the neurodegenerative disease, Alzheimer's disease (AD), which is characterized by the deposition of—amyloid peptides in neural tissue, leading to neuronal cell degeneration, cell death and progressive dementia.

The present invention also relates to methods of evaluating the risk of an individual to develop Alzheimer's disease using an in vitro assay system comprising epidermal melanocytes obtained from the individual. Epidermal melanocytes are melanocytes found in the epidermis (skin) and hair bulbs of vertebrates. The present invention is based on Applicants' findings that human melanocytes exhibit significant similarities with central nervous system neurons (the cells predominantly affected by Alzheimer's disease) and that melanocytes utilize the same signaling molecules as neurons to determine their survival versus programmed cell death (apoptosis).

For example, neuronal cells express a high affinity ($p_{140}^{trkA}$) and a low affinity receptor ($p75^{NTR}$) for nerve growth factor (NGF). As described herein, Applicants have demonstrated that these nerve growth factor receptors are also expressed on melanocytes and that β-amyloid binds to the low affinity nerve growth factor receptor, $p_{75}^{NTR}$, expressed on the melanocyte surface. Applicants also demonstrate herein that binding of β-amyloid to the $p75^{NTR}$ activates the receptor, resulting in apoptotic cell death of the melanocytes. Applicants further demonstrate that the β-amyloid mediated-apoptosis can be competitively blocked by providing nerve growth factor or a biologically active fragment, analog or derivative thereof. Nerve growth factor is a physiologic ligand for $p75^{NTR}$ that has a 2–3-fold higher receptor affinity than β-amyloid and when binding coordinately to $p_{75}^{NTR}$ and $p140^{trkA}$, exhibits a 200-fold higher affinity Additionally, Applicants have demonstrated that melanocytes secrete β-amyloid (in the form of its precursor protein) constitutively, and in increased amounts in response to trauma, e.g., UV irradiation. Thus, based on results described herein, Applicants have established that melanocytes, easily obtainable from skin biopsies, are reasonable model cells for the study and diagnosis of Alzheimer's disease.

Based on the results described herein, neuronal cell death resulting in Alzheimer's Disease can arise in several different settings. For example, if an excess of β-amyloid protein is present in the central nervous system (CNS), more β-amyloid protein will bind to the $p75^{NTR}$ and initiate the apoptotic pathway-in cells. Nerve growth factor binds to two receptors on the cell surface, $p75^{NTR}$ and $p140^{trkA}$. Nerve growth factor binding to both of these receptors leads to the transmission of a cell survival signal. If excess amounts of the $p75^{NTR}$ are expressed on cells, more β-amyloid can bind to the $p75^{NTR}$ even in the presence of NGF and initiate the cell death pathway. If insufficient $p140^{trkA}$ is expressed, which results in an excess of $p75^{NTR}$ on the cell surface, or if insufficient nerve growth factor ligand is available to bind to the $p75^{NTR}$, β-amyloid can then also bind to the excess $p75^{NTR}$, leading to cell death. All of the above, or any combination of the above, can lead to apoptosis and AD.

In the proposed diagnostic test, ease of induction of melanocyte apoptosis in vitro following exposure to β-amyloid protein and/or the blocking of this apoptosis by nerve growth factor (NGF) supplementation is correlated with the predisposition of the cell donor to develop Alzheimer's disease. Melanocytes obtained from a patient's skin biopsy are compared to standardized control cell lines. β-amyloid protein or peptide is introduced into the cultures and melanocyte apoptosis resulting from binding of the β-amyloid protein to the $p75^{NTR}$ is determined. Activation of the $p75^{NTR}$ by binding of the $p75^{NTR}$ by β-amyloid protein, or peptide, results in apoptotic cell death of the melanocytes. Thus, activation of the $p75^{NTR}$ by β-amyloid can be measured quantitatively as apoptotic cell death of the melanocytes. Apoptotic cell death is readily assessed by any of a number of standard parameters such as propidium iodine incorporation into nuclear fragments, labeling of DNA strand breaks using fluorescein tagged dUTP in the presence of terminal deoxynucleotidyl transferase (TUNEL reaction), or by demonstration of fragmented DNA (a DNA ladder). Apoptosis can also be measured by cell counts that reveal progressive cell death. The activation of the $p75^{NTR}$ expressed on the melanocytes obtained from the individual suspected of having AD is compared with the activation of the $p75^{NTR}$ expressed on control melanocytes. If the activation of the $p_{75}^{NTR}$ on the individual's melanocytes is greater than the activation of the $p75^{NTR}$ on the control melanocytes, it is indicative of the greater risk of the individual to develop Alzheimer's disease.

The present invention also relates to methods of treating, or reducing the risk of developing, Alzheimer's disease, or other neurodegenerative diseases associated with the β-amyloid protein, or by the activation of the $p75^{NTR}$ resulting in apoptotic neural cell death. In the proposed therapy for Alzheimer's disease, a composition containing the tripeptide lysine-glycine, lysine, lysine-glycine-alanine or a similar peptide with established affinity for the $p75^{NTR}$ would be delivered by an appropriate route (e.g., intravenously with an agent to reduce the blood-brain barrier or intraventricularly) to central nervous system neurons at risk of β-amyloid induced apoptotic cell death to block β-amyloid binding to $p75^{NTR}$. Nerve growth factor (NGF), biologically active fragments, analogs or derivatives of NGF (wherein biological activity is defined herein as the ability of the fragment, analog or derivative to bind to the $p75^{NTR}$ expressed on neural derived cells such as neurons and melanocytes) and/or other neurotropins could also be-administered to further compete against β-amyloid binding to $p75^{NTR}$, as well as to activate cell survival programs within damaged neurons, for example through upregulation of the apoptosis-inhibiting protein, Bcl-2. The therapeutic peptide is designed to have a receptor affinity comparable to, or greater than, that of β-amyloid but less than that of NGF and other neurotrophins. Typically, the peptide will be a cyclic, or β-loop configuration.

Other methods encompassed by the present invention include methods of decreasing, or inhibiting the expression of $p75^{NTR}$ by contacting cells expressing the receptor wtih an anti $p75^{NTR}$ anti sense nucleic acid, thereby decreasing or inhibiting the expansion of $p75^{NTR}$ on the cells, thus reducing the risk of β-amyloid mediated apoptosis. Anti-sense $p75^{NTR}$ nucleic acid molecules can be produced by one of skill in the art using the nucleotide sequence of $p75^{NTR}$ as described in Johnson, D., et al., Cell,. 47:545–554 (1986).

Alzheimer's disease is a devastating and ultimately fatal disorder. Early detection of Alzheimer's disease would make possible early intervention to prevent, or substantially reduce, neuron degeneration and death. Currently, therapies to treat Alzheimer's disease are minimally effective. As effective treatments become available, it would permit rational therapy from an early point in the disease process when secure diagnosis by conventional clinical criteria is rarely possible. Availability of a therapeutic substance that could slow the progression of Alzheimer's disease, or other neurodegenerative diseases, in affected patients would be a great boon to those individuals.

DETAILED DESCRIPTION OF THE INVENTION

The present invention is based on Applicants' finding that melanocytes are neural crest-derived cells that share many signal transduction pathways with central nervous system neurons, including the high and low affinity receptors for nerve growth factor (Peacocke, M., et al., Proc. Natl. Acad. Sci. USA, 85:5282–5286 (1988); Yaar, M., et al., J. Cell. Biol., 115:821–828 (1991); Yaar, M., et al., J. Clin. Invest., 94:1550–1562 (1994) basic fibroblast growth factor (Halaban, R., et al., J. Immunother., 12:154–161 (1992), and other molecules. Based on these significant similarities with neurons, it is demonstrated herein that cultured human melanocytes provide a model system for studies of Alzheimer's disease.

More specifically, the present invention relates to an in vitro method of evaluating the risk of an individual to develop Alzheimer's disease mediated by β-amyloid protein using cultured epidermal melanocytes obtained from the individual. The present invention also relates to the use of a melanocyte cell culture model or a tissue biopsy sample to evaluate therapeutic compounds effective in the treatment of Alzheimer's disease, and other neurodegenerative diseases mediated by β-amyloid protein. The methods of the present invention are based on Applicants' finding that β-amyloid protein binds to the 75 kilodalton (kD) neurotrophin receptor ($p75^{NTR}$) (also referred to herein as the low affinity nerve growth factor receptor, or p75 nerve growth factor receptor) which is expressed on the surface of both melanocytes and central nervous system neurons, and that when the $p75^{NTR}$ is bound by β-amyloid, a pathway resulting in cell death (apoptosis) is activated. Applicants further demonstrate herein that this activation can be blocked by substances (e.g., cyclic peptides) that also bind the $p75^{NTR}$, competitively block β-amyloid binding and, hence, prevent cell death.

MELANOCYTES PROVIDE A MODEL SYSTEM FOR ALZHEIMER'S DISEASE

In vitro studies have demonstrated that β-amyloid protein plays a central role in Alzheimer's disease. Attempts to understand the pathophysiology of Alzheimer's disease using malignant cell lines (Boland, K., et al., J. Biol. Chem., 270:28022–28028 (1995) or vertebrate neuronal cell cultures (Mark, R. J., et al., J. Neurosci., 15:6239–6249 (1995) have revealed that supplementation with β-amyloid peptides composed of amino acid residues 1 to 40 or 25 to 35 of the β-amyloid protein result in neurotoxicity and cell death. In particular, β-amyloid peptide comprising amino acid residues 1–40 of the β-amyloid protein, amino acid residues 1–42, or, more specifically, amino acid residues 25–35 result in neurotoxicity and neuronal cell death. Recent studies have also shown that β-amyloid-induced neurotoxicity exhibits classic features of apoptosis. The β-amyloid precursor protein (also referred to herein as βAPP) is widely expressed in neural and nonneural mammalian tissues. βAPP is most highly expressed in brain and kidney, and in the w brain, neurons demonstrate particularly high expression of βAPP.

Applicants have demonstrated that human melanocytes and cells of melanocytic origin also constitutively synthesize and secrete βAPP. After cellular trauma such as ultraviolet irradiation, there is increased βAPP secretion, leading to increased βAPP concentration in the vicinity of cultured cells (Andersen, W., et al., J. Invest. Dermatol., 104:585 Abst.182 (April 1995). Such increased βAPP secretion may also be presumed to occur when neurons are injured.

Applicants demonstrate herein that supplementation of normal human melanocytes with β-amyloid 1–40 peptide at low concentrations (≦1 μM) leads to extensive outgrowth of dendrites, the melanocyte cell processes analogous to neurites of neurons, often a marker of mild injury for which the cell can compensate, without decreasing cell yields. At higher concentrations of β-amyloid peptide, melanocyte cell yields decrease progressively and the remaining cells appear unhealthy. Additionally, in these cultures there is focal development of plaque-like structures consisting of aggregated dying melanocytes, similar to the in vivo "senile plaques" observed in patients with AD.

Applicants further demonstrate herein that maintaining melanocytic cell cultures in ≧25 μM β-amyloid 1–40, compared to control cultures, significantly increases the proportion of apoptotic cells and upregulates Bax protein expression approximately three fold. Recent in vivo and in vitro data suggest that the β-amyloid induced-neuronal death exhibits classical characteristics of programmed cell death or apoptosis (Cotman, C. W. and Anderson, A. J., *Mol. Neurobiol.*, 10:19–45 (1995); Su, J. H., et al., *Neuroreport*, 5:2529–2533 (1994). The molecular pathways that regulate apoptosis in neurons have been identified in part. Evidence suggests that the product of the proto-oncogene Bcl-2 delays the onset of apoptosis in neurons that are dependent for survival on neurotrophic factors (Allsopp, T. E., et al., *Cell*, 73:295–307 (1993); Garcia, I., et al., *Science*, 258:302–304 (1992). Conversely, overexpression of a 21 kD Bcl-2-associated protein, Bax, accelerates apoptotic death of cells (Oltvai, Z. N, et al., *Cell*, 74:609–619 (1993)).

Melanocytes express both the low affinity $p75^{NTR}$ and high affinity 140 kD trk A ($p_{140}^{trkA}$) receptors for NGF. Providing NGF to melanocytes results in activation of the $p_{140}^{trkA}$ pathway, presumably through co-ordinate binding of $p_{140}^{trkA}$ and multiple $p75^{NTR}$ molecules as postulated to occur in neurons exposed to NGF, that in turn activates an intracellular signal transduction pathway leading to enhanced expression of Bcl-2 and enhanced cell survival. Applicants have also demonstrated, using melanocytes from newborn, young adult and old adult donors, that there is a prominent increase in the expression of the apoptotic $p75^{NTR}$ with aging.

Applicants demonstrate herein that β-amyloid binds competitively to the $p75^{NTR}$. Studies previously published suggest that the specific binding site for the $p75^{NTR}$ is amino acids 29–36 of the NGF protein (Ulrich, A., et al., *Nature* 303:821–825 (1983), and that if the sequence lysine-glycine-lysine (residues 32–34 of NGF) is changed to lysine-glycine-alanine, the peptide has approximately half the affinity for the receptor as native NGF. Amino acid residues 28–30 of the β-amyloid protein are lysine-glycine-alanine. Furthermore, computerized structure analysis of β-amyloid reveals that these amino acids have a high probability of being in a loop turn of the protein, suggesting a high probability that this β-amyloid peptide sequence plays a role in receptor binding.

A cyclic decapeptide was therefore synthesized by attaching two cysteine residues to the beginning and the end of the β-amyloid fragment consisting of amino acids 24–31: VGSNKGAI (SEQ ID NO: 1). Cold peptide competitively inhibited $^{125}$I-β-amyloid binding, with 50% inhibition occurring at 25 nM. Furthermore, β-amyloid at a concentration of 200 nM reduced by cell yields by ~60% (p<0.02), but this cell loss was blocked by the peptide (200 nM). Peptide alone had no effect on cell yield. These findings indicate that apoptosis of neurons in Alzheimer's Disease results from the interaction of β-amyloid with $p75^{NTR}$. The data also suggest that β-amyloid-mediated death of neurons may be prevented by delivery of a synthetic peptide, in the proper conformation, that blocks the β-amyloid binding sites.

Thus, the above findings of significant similarities of CNS neurons and epidermal melanocytes, permitting their use in diagnostic testing and drug development studies for Alzheimer's disease.

IN VITRO ASSAY FOR ALZHEIMER'S DISEASE

The melanocyte model system described herein can be used for the early identification of individuals who are at risk for developing Alzheimer's disease. At present, there are three known or suspected mechanisms for the development of Alzheimer's disease: 1.) Increased production and/or secretion of β-amyloid by CNS neurons, a dysfunction known to result from one of the recognized βAPP mutations in familial Alzheimer's disease patients; 2.) Increased sensitivity to physiologic β-amyloid concentration due to excessive local aggregation of the β-amyloid peptide for as yet unknown reasons, speculated to result from subtle structural alterations in the secreted β-amyloid or from subtle abnormalities of the extracellular matrix in the CNS; and 3.) Decreased expression or function of the low density lipoprotein receptor-related protein on the surface of neurons that is known to bind, internalize, and degrade βAPP and whose functional deficiency would result in increased amounts of extracellular β-amyloid.

Melanocytes are isolated from skin biopsies obtained from the individual to be tested, i.e., test melanocytes. Skin biopsies are performed using standard dermatological techniques. Typically, after application of a local anesthetic, a 3–4 mm punch biopsy is obtained from the skin of the individual. Any convenient skin site for biopsy can be selected. Melanocytes isolated from skin are also referred to herein as epidermal melanocytes.

The melanocytes obtained from the individual are cultured under standard laboratory conditions as described herein, typically using serum-free medium. Control cultures of melanocytes are also maintained under similar conditions. Control melanocytes can be obtained from an individual known to be disease-free, from neonatal foreskins, or from available melanocyte cell lines. (See, e.g., Park, H-Y. et al., *J. Biol. Chem.*, 268:11742–11749 (1993)). All melanocytes express the $p75^{NTR}$ plus $p140^{trkA}$ receptor proteins. The cultures are maintained under these conditions for approximately two days to ensure stable, viable melanocyte cultures. The cultures can be maintained for longer time periods as long as the melanocytes remain viable.

After culture stabilization β-amyloid protein or β-amyloid peptide is introduced into the cultures. As defined herein, β-amyloid protein includes β-amyloid precursor protein as well as β-amyloid protein. β-amyloid peptide includes β-amyloid 1–40 peptide; β-amyloid 1–42 peptide; β-amyloid 25–36 peptide and β-amyloid 28–30 peptide. β-amyloid proteins and peptides are commercially available from various sources, e.g, Bachem Calif., Torrance, Calif. β-amyloid protein and peptides can also be chemically synthesized or recombinantly produced using known laboratory techniques. The β-amyloid protein or peptide introduced into the culture is typically dissolyed in a buffer compatible with the cell culture medium. The concentration of β-amyloid protein or peptide added to the culture can vary from 0 μM to 100 μM, typically from 1 μM to 50 μM. A typical single dose of β-amyloid protein or peptide is approximately 25 μM. The concentration of β-amyloid protein or peptide added is a concentration sufficient to bind to, and activate the $p75^{NTR}$ As defined herein, activation of the $p75^{NTR}$ by β-amyloid protein or peptide means the initiation, or activation of the apoptotic cell death pathway in the elanocyte. As further defined herein, the activation of the $p75^{NTR}$ also means the induction of Bax protein or the initiation of sphingomyelin hydrolysis.

The melanocyte cultures are maintained in the presence of β-amyloid protein or peptide for a time sufficient for detectable activation of the $p75^{NTR}$ to occur, typically about three days. However, the time can be as short as 1 or as long as 8 days. The activation of the $p75^{NTR}$ of the test melanocytes is compared with the activation of the $p75^{NTR}$ of the control melanocytes.

The activation of the $p75^{NTR}$ by β-amyloid results in apoptotic cell death of the melanocytes. Apoptosis is determined using well-known laboratory techniques. As described herein in Example 1, an assay to determine melanocyte cell yield was used to determine apoptosis. Apoptosis decreases cell yield. Cell yield is determined by counting viable cells, such as with an electronic cell counting instrument (e.g., a Coulter™ cell counter) or by performing a manual cell count using a hemocytometer.

Also as described in Example 1, the cultures can be microscopically evaluated for the presence of plaque-like structures containing dying, and/or dead melanocytes. These plaques also contain β-amyloid deposits.

As described in Example 2, activation of the $p75^{NTR}$ can also be determined using an assay to measure the inducement of Bax protein expression. Bax is the Bcl-2-associated protein implicated in the apoptotic cell death pathway. An increase in the expression of Bax is an indication of apoptosis. Measurement of Bax protein expression can be accomplished by determining the increase of Bax mRNA expressed in the cells, using standard laboratory techniques to determine RNA in cells. Bax inducement can also be measured using anti-Bax antibody in Western blot analysis.

Apoptosis can also be determined by the measurement of propidium iodine incorporation into nuclear fragments, the TUNEL reaction, demonstration of fragmented DNA, or cell count.

If the activation of the $p75^{NTR}$ of the test melanocytes is greater than the activation of the $p75^{NTR}$ of the control melanocytes, it is an indication that the individual from whom the test melanocytes were obtained has neural crest cells that are more sensitive than standardized control cell lines to β-amyloid. If the individual's neural crest cells are more sensitive to β-amyloid, it is reasonable to predict that the individual is at risk to develop Alzheimer's disease. In individuals whose melanocytes exhibit abnormal sensitivity to β-amyloid, further characterization of the synthesis and deposition of extracellular matrix molecules can be performed using the melanocyte culture method to determine the interaction of these extracellular molecules with the β-amyloid peptide.

The cultured melanocyte assay method described herein can also be useful to evaluate the function of the low density lipoprotein receptor-related protein on the patient's neural crest cells.

Neurons constitutively secrete β-amyloid precursor protein. Because β-amyloid is a major component of the hallmark senile plaques found in Alzheimer's disease patients, the presence of increased levels of β-amyloid protein and/or peptide surrounding neurons is reasonably correlated with the presence of Alzheimer's disease. Using the melanocyte culture assay method described herein, it can be determined if the patient's neural crest cells synthesize and/or secrete increased levels of β-amyloid constitutively or in response to trauma, in greater amounts as compared to standardized control cell lines. If the secretion of β-amyloid protein or peptide is greater in the test melanocyte culture than in the control melanocyte culture it is indicative that the individual has an increased risk of developing Alzheimer's disease.

As described above, a number of pathologic mechanisms leading to Alzheimer's disease are known or suspected. As described herein, Applicants demonstrate that the final pathway upon which all the above mechanisms converge is the activation of the $p75^{NTR}$ alone, leading to apoptosis, instead of the beneficial activation of a receptor complex consisting of NGF, $p75^{NTR}$ and $p140^{trkA}$ Therefore, the determination of the individual's risk developing Alzheimer's disease can be accomplished by measuring levels of $p75^{NTR}$ versus $p140^{trkA}$ expressed on the surface of the individual's melanocytes. Individuals with a high ratio of $p75^{NTR}$ to $p140^{trkA}$ would be those at risk for developing Alzheimer's disease. Specimens obtained from individuals to be tested can be prepared for immunochemistry, in-situ hybridization or in-situ PCR, as described herein, to quantitate the expressed receptors. For example, the method of evaluating the risk of an individual to develop Alzheimer's disease associated with β-amyloid protein or β-amyloid peptide activation of the p75 nerve growth factor receptor comprises the steps of obtaining a skin specimen containing melanocytes from the individual and processing the specimen to render it suitable for either immunohistochemistry, in situ hybridization or in situ PCR. For immunohistochemistry, the specimen is contacted with an anti-$p75^{NTR}$ antibody and incubated under conditions suitable for the antibody to bind to the $p75^{NTR}$ present in the melanocytes in the specimen. The level of bound antibody is measured and therefore the level of $p75^{NTR}$ in the specimen is quantified, using methods well known in the art. An increase in the level of $p75^{NTR}$ as compared to an age-matched control specimen is an indication that the individual is at risk for Alzheimer's disease.

For in situ hybridization, the specimen is contacted with a labeled nucleic acid probe comprising a nucleic acid sequence encoding all or a portion of the $p75^{NTR}$, (Johnson, D., et al., Cell, 47:545–554 (1986)) under conditions suitable for hybridization of the probe with nucleic acid encoding $p75^{NTR}$ present in the melanocytes the specimen. The level of hybridized probe, and therefore the level of $p75^{NTR}$ in the specimen is quantified using methods well known in the art. An increase in the level of $p75^{NTR}$ as compared to an age-matched control specimen is an indication that the individual is at risk for Alzheimer's disease.

For in situ PCR, the specimen is contacted with nucleic acid primers comprising a nucleic acid sequence encoding the $p75^{NTR}$ under conditions suitable for the amplification nucleic acid encoding $p75^{NTR}$ present in the melanocytes the specimen. The level of amplified sequence and therefore the level of $p75^{NTR}$ in the specimen is quantified using methods well known in the art. An increase in the level of $p_75NTR$ as compared to an age-matched control specimen is an indication that the w individual is at risk for Alzheimer's disease.

Thus, using the methods described herein, it is reasonable to predict whether an individual is at risk to develop Alzheimer's disease. Moreover, using the methods of the present invention it is also reasonable to predict by what mechanism given individuals are likely to develop the disease, e.g., abnormal sensitivity β-amyloid, increased secretion of β-amyloid protein, or abnormal ratio of expressed $p75^{NTR}$ to $p140^{trkA}$, and thus allow selection of a therapeutic approach that specifically targets the abnormality. Furthermore, the method of the present invention is useful to screen therapeutic substances, as described below, to determine their effectiveness in an individual. Thus, an individual with either a known predisposition to Alzheimer's disease, or a diagnosis of Alzheimer's disease based on conventional clinical criteria, will be treated with a substance of demonstrated in vitro efficacy, and thus, increase chances of alleviating the disease symptoms.

EVALUATION OF EFFECTIVE ALZHEIMER'S DISEASE THERAPIES

NGF binds two receptors: the protein product of the trkA proto-oncogene, $p_{140}^{trkA}$, a transmembrane tyrosine kinase receptor, and a 75 kD low affinity transmembrane receptor for several neurotrophins, $p75^{NTR}$ $p_{140}^{trkA}$ has been reported to mediate NGF-induced effects in the absence of $p75^{NTR}$ (Verdi, J. M., et al., *Proc. Natl. Acad. Sci. USA*, 91:3949–3953 (1994)). It has also been reported that $p75^{NTR}$ mediates apoptosis of developing neurons in the absence of trkA and that modulation of $p75^{NGF}$ receptor can promote neuronal survival (Catharina, F. E., *Science*, 1725:1729–1732 (Dec.6, 1996)). However, the functional importance of $p75^{NTR}$ in NGF signal transduction is still controversial. It was reported that co-expression of $p75^{NTR}$ and $p140^{trkA}$ produces functional high-affinity binding of NGF (Battleman, D. S., et al., *J. Neurosci.*, 13:941–951 (1993)). It was also reported that activation of $p75^{NTR}$ in cells that do not express $p_{140}^{trkA}$ induces their apoptosis by activation of the sphingomyelin signaling pathway. It is therefore possible that $p75^{NTR}$ has a dual role. In combination with $p140^{trkA}$ it may signal through a tyrosine kinase-dependent pathway (Dobrowsky, T. T., et al., *Science*, 265:1596 (1994) leading to survival, but when activated alone it signals through the sphingomyelin pathway leading to apoptosis.

Binding of NGF to $p75^{NTR}$ is mediated through amino acid residues 29–36, TDIKGKEV (SEQ ID NO: 2), that are part of the β-hairpin loop of NGF (Ibánez, C. F., et al., *Cell*, 69:329–341 (1992)). If lysine (K) at position 34 is replaced by alanine (A), the resulting mutant NGF molecule still binds $p75^{NTR}$ but with 50% lower affinity. Interestingly, in β-amyloid the amino acid residues 28–30, which are present in both the 1–40 and the 25–35 β-amyloid peptides, are KGA, a sequence that appears to permit $p75^{NTR}$ binding by β-amyloid. Computerized structure analysis of β-amyloid suggests that the KGA residues have a high probability (>60%) of being in a loop turn, the highest probability of any portion of this 40 amino acid peptide, suggesting that this sequence constitutes a binding site for $p75^{NTR}$. Furthermore, it was reported that expression of $p75^{NTR}$ enhances the toxic effect of β-amyloid on cells, possibly through binding and activation of the receptor.

Based on the above data, it is reasonable to believe that the specific three amino acid sequence lysine-glycine-alanine (KGA) in the β-amyloid protein binds the 75 kD transmembrane neurotrophin receptor on CNS neurons, activating the programmed cell death pathway, mediated in part by an increase in intracellular Bax levels.

It is also reasonable to believe that competitively inhibiting the binding of β-amyloid peptide blocks this aberrant receptor activation and the resulting apoptosis. For example, providing full-length NGF, or a biologically active fragment, analog, derivative, variant or mutant thereof results instead in preferential binding of $p75^{NTR}$ coordinately with $p140^{trkA}$ binding, leading to activation of a second signal transduction pathway that results in neuronal cell survival. Such a biologically active NGF fragment would contain the amino acid sequence, lysine-glycine-lysine (KGK).

The term "biological activity" of NGF, or a fragment, derivative, analog, variant or mutant NGF, is defined herein as the activity of the NGF to specifically bind to the $p75^{NGF}$ receptor. Such activity can be measured by the methods described herein, or by other methods known to those skilled in the art. Another biological activity of an NGF fragment, analog, derivative, variant or mutant is the antigenic property of inducing a specific immunological response as determined using well-known laboratory techniques. For example, a biologically active NGF fragment can induce an immunological response which produces antibodies specific for the NGF (anti-NGF antibodies).

An "analog" is defined herein to mean an amino acid sequence with sufficient identity to amino acid sequence of the endogenous NGF to possess the biological activity of the protein. For example, an analog of a polypeptide can have introduced into the polypeptide amino and sequence "silent" changes wherein one or more amino acid residues differ from the amino acids residues of the NGF yet still possess $P75^{NTR}$ binding activity. Examples of such differences include additions, deletions, or substitutes of residues. Also encompassed by the present invention are proteins that exhibit lesser or greater biological activity of NGF.

The present invention also encompasses the production and use of biologically active fragments of the NGF described herein. Such fragments can include only a part of the full length amino acid sequence of NGF, yet possess biological activity. As used herein, the term "biologically active fragment" means NGF a fragment that can exert a biological or physiologic effect of the full-length protein, or has a biological characteristic, e.g., antigenicity, of the full-length protein. Such activities and characteristics are described herein. Such fragments can be produced by amino and carboxyl terminal deletions as well as internal deletions. Also included are active fragments of the protein, for example, as obtained, by enzymatic digestion. Such peptide fragments can be tested for biological activity.

"TDerivatives" and "variants" of NGF is NGF which has been modified. This includes NGF which have been modified by alterations in the amino acid sequence associated with the $p57^{NTR}$. This also includes, but is not limited to, truncated and hybrid forms of NGF. "Truncated" forms are shorter versions of NGF, for example, modified so as to remove the C-terminal regions. "Hybrid" forms include NGF that is composed of portions of two or more proteins, i.e., a fusion protein comprising NGF with another protein.

Variants can be produced using the methods known to those of skill in the art. The NGF gene can be mutated in vitro or in vivo using techniques known in the art, for example, site-specific mutagenesis and oligonucleotide mutagenesis. Manipulations of the NGF sequence can be made at the protein level as well. Any of numerous chemical modifications can be carried out by known techniques including, but not limited to, specific chemical cleavage by cyanogen bromide, trypsin, and papain. It can also be structurally modified or denatured, for example, by heat or by being immobilized on a solid surface.

The amino acid sequences of the NGF fragments, analogues, derivatives, variants and mutants of the present invention can be altered to optimize NGF binding to $p75^{NTR}$, by methods known in the art by introducing appropriate nucleotide changes into native or variant DNA encoding the NGF, or by in vitro synthesis of the desired NGF.

It is reasonable to assume that NGF has a higher affinity for the $p75^{NTR}$ than does β-amyloid, and that when NGF is present in the cellular environment, this neurotrophin preferentially binds the p75$^{NTR}$ coordinately with the p140$^{trkA}$ receptor, activating p140$^{trkA}$ and leading to cell survival. However, under conditions leading to increased surface expression of p75$^{NTR}$ or increased levels of β-amyloid in the extracellular space, in the absence of saturating amounts of NGF, apoptotic cell death may result from binding of β-amyloid to the p75$^{NTR}$ with subsequent activation of the sphingomyelin pathway. In the CNS, such a situation might occur in older individuals, particularly those with a genetically-determined excessive production of β-amyloid fragments containing the amino acid sequence required for p75$^{NTR}$ binding. Normal human melanocytes appear to respond to environmental signals in the same manner as CNS neurons and reasonably provide a model system for studying potential therapies for Alzheimer's disease.

Thus, the present invention also encompasses methods employing melanocyte for the development and evaluation of substances to enhance cell survival and to block β-amyloid-induced apoptotic cell death. Specifically, the methods of the present invention can be used to identify and evaluate substances to treat Alzheimer's disease. For example, the melanocyte culture model can be used to identify substances that block the p75$^{NTR}$ binding of β-amyloid, and thus block β-amyloid-mediated neuronal apoptosis. Several assay methods are available in the art to measure p75 nerve growth factor receptor activation by β-amyloid protein or β-amyloid peptide and include an assay to determine melanocyte cell yield, an assay to determine the inducement of Bax protein expression; an assay to determine the onset of melanocyte apoptosis or an assay to determine the presence of plaque-like structures in the melanocyte culture. Methods to determine the onset of melanocyte apoptosis are well known in the art and include measurement of propidium iodine incorporation into nuclear fragments, the TUNEL reaction or demonstration of fragmented DNA. In addition, in the method of the present invention, a series of multiple cultures of the neural crest-derived cells is maintained; the test substance is added to each culture such that each culture in the series receives an increasing concentration of test substance ranging from about 10 μM to about 100 μM. The activation of the p75 nerve growth factor receptor is determined and correlated to the concentration of test substance added. Furthermore, as described in the Examples, inhibition of β-amyloid protein or β-amyloid peptide binding to the p75 nerve growth factor receptor can be measured using standard competition assays.

Candidate substances that inhibit the binding of β-amyloid protein/peptide can also be identified using other cells expressing p75$^{NTR}$. Such cell lines can be engineered to transitionally or stably express p75$^{NTR}$ (M. Yaar and B. A. Gilchrest, *Arch. Dermatol.*, 133:1287–1291 (1987).

Furthermore, candidate substances that inhibit the binding of amyloid protein/peptide can also be identified using in vitro binding assays well known in the art, such as surface plasmon resonan (SPR). For example, peptide libraries and other small organic molecule libraries can be screened using proximity assays or Biospecific Interaction Analysis (BIA). Biospecific Interaction Analysis (BIA) in real time can be performed to evaluate candidate molecules for their ability to bind p75$^{NTR}$ T Surface plasmon resonance (SPR), which is the basis for BIA measurements, is an optical phenomenon arising in metal films under conditions of total internal reflection. The phenomenon produces a sharp dip in the intensity of reflected light at a specific angle. The position of this resonance angle depends on several factors, including the refractive index of the medium close to the non-illuminated side of the metal film. Refractive index is directly related to the concentration of dissolyed material in the medium. By keeping other factors constant, SPR is used to measure changes in the concentration of macromolecules in a surface layer of solution in contact with a dextran-coated gold film. Using the BIAcore™ instrument from Pharmacia Biosensor AB, the association and dissociation rate constants for a peptide or organic molecule binding to p75$^{NTR}$ can be measured. Polypeptides peptides, peptide mimics or small organic molecules exhibiting higher association constants ($K_a$) have the greatest potential for ability to interact with p75$^{NTR}$ and inhibit β-amyloid protein/peptide binding to p75$^{NTR}$.

As described above, the tripeptide lysine-glycine-alanine is a candidate substance for use as a therapeutic to alleviate the symptoms of Alzheimer's disease. The melanocyte culture model system can be used to identify and evaluate other peptides containing the KGK or KGA sequence, or various analogs of the KGK or KGA tripeptide, to determine an optimum conformation and composition that will bind p75$^{NTR}$ and, thus, block the binding of the apoptosis-inducing β-amyloid ligand without interfering with NGF binding that is beneficial. Because evaluation of candidate substances is made with melanocytes obtained specifically from the individual at risk, or with the diagnosis of AD, the probability of identifying an effective candidate substance is very high.

Once candidate substances are identified, the therapeutic level of substance that must be delivered to the CNS can be accurately determined using in vitro melanocyte cultures from each individual. Titration of concentration of the candidate substance can be performed using the melanocyte culture model system described herein.

Also encompassed by the present invention are methods of therapy for the treatment of neurodegenerative diseases resulting from apoptosis due to the aberrant activation of the p75$^{NTR}$ receptor of neural crest-derived cells, or increased expansion of the p75$^{NTR}$. Specifically encompassed are methods of therapy for individuals experiencing symptoms of dementia resulting from degeneration, and death, of neurons due to β-amyloid-mediated apoptosis. β-amyloid-mediated apoptosis is a hallmark of Alzheimer's disease, therefore, also specifically encompassed by the present invention are methods of treating individuals with Alzheimer's disease.

Methods of therapy include administering to the individual a substance, e.g., a cyclic peptide comprising KGK or KGA, or an analog thereof, in a manner which permits contact of the substance with neurons of the CNS. For example, the pentapeptide CKGAC (SEQ ID NO: 3), or an analog thereof, can be chemically synthesized by methods well-known to one of skill in the art. The cysteine residues flanking the ends of the pentapeptide can be linked, e.g., by a disulfide bond, to maintain the conformation required for binding of the peptide to the p75$^{NTR}$, thus inhibiting, or preventing apoptosis. The length of the peptide can be longer than a pentapeptide, as long as the KGA, or analog peptide is maintained in a configuration suitable for binding activity. For example, as described herein, cyclic peptides have been made with the amino acid sequences and CVG-SNKGAIC (SEQ ID NO: 4) these peptides compete for p75$^{NTR}$. binding with β-amyloid peptide. It is reasonable to believe that other cyclic peptides would also bind p75$^{NTR}$ and inhibit apoptosis. Administration, or delivery of the peptide, or other substance, can be accomplished in a manner similar to methods used in gene transfer and therapy. For example, an effective amount of the DNA encoding the peptide can be inserted into a virus vector construct which targets central nervous system neurons. The DNA insert also includes sequences necessary for the expression of the DNA in the target cells. Particularly useful is the Herpes Simplex Virus-1 (HSV-1) vector described in Geller, A. I., and Breakefield, X. O., *Science* 241:1667–1669 (1988) and U.S. Pat. No. 5,288,641 (Roizman 1994), the teachings of these references are herein incorporated by reference. Gene guns can also be used. Additionally, intracranial administration can be employed.

Further in vivo testing cam be performed using an art-recognized mouse model such as the transgenic mouse described in WO 96/40895, the teachings of which are incorporated herein by reference. Such testing is well-known to those of skill in the art.

The following examples more specifically illustrate the invention and are not intended to be limiting in any way.

EXAMPLE 1

THE EFFECT OF β-AMYLOID ON NORMAL HUMAN MELANOCYTES

To determine the effect of β-amyloid on normal human melanocytes, cultures were supplemented with increasing concentrations (0.025–50 uM) of HPLC-purified β-amyloid fragment corresponding to amino acids 1–40. A peptide containing the first 40 amino acids synthesized in reverse order (40–1) was used as a negative control.

Melanocytes were maintained in serum free Medium 199 (Gibco BRL Gaithersburg, Md.) supplemented with epidermal growth factor (10 ng/ml) (Collaborative Research), insulin (10 µg/ml) (Sigma), triiodothyronine ($10^{-9}$ M) (Collaborative Research), transferrin (10 µg/ml) (Sigma), hydrocortisone ($1.4 \times 10^{-6}$ M) (Calbiochem), cholera toxin ($10^{-9}$ M) (Calbiochem) and basic fibroblast growth factor (basic FGF) (10 ng/ml) (Collaborative Research). Two days after plating cells were supplemented with increasing concentrations of β-amyloid 1–40 or the control peptide 40–1 (0–50 µM) (Bachem Calif., Torrance, Calif.). Cell yields determined three days after addition of β-amyloid show a dose dependent decrease of cell yield in cultures maintained with the 1–40 peptide. No effect on cell yield was observed in cultures maintained with the control 40–1 peptide.

Melanocytes maintained in the presence of 25–30 uM β-amyloid 1–40 showed a 59% ±17% decrease in cell yield as compared to cell yield before β-amyloid addition that is considered to be 100%. Cell yield of duplicate cultures maintained in the presence of the control 40–1 peptide showed 8%±32% increase in cell yield (p<0.02, paired t test).

Melanocytes maintained in the presence of the 40–1 control peptide have a typical bipolar to polygonal morphology. The majority of the melanocytes maintained in the presence of the 1–40 peptide are rounded and detaching from the dish surface.

Regression analysis showed significant decrease in cell yield with increasing concentrations of β-amyloid 1–40 ($R^2$=0.8475, p<0.00001) but no significant effect on cell yield of β-amyloid 40–1 ($R^2$=0.06, p=0.44). In a total of four experiments, within 3–5 days ,-amyloid 1–40 decreased melanocyte yield by >50% (p<0.02; paired t test) while the control 40–1 β-amyloid peptide at the same concentrations had no effect on cell yield.

EXAMPLE 2

EFFECT OF β-AMYLOID 1–40 ON MELANOCYTE PLAQUE FORMATION

Melanocyte cultures, cultured as described above in Example 1, were also evaluated for plaque formation. In some cultures the development of plaque-like structures consisting of increasingly large congregations of dying melanocytes was noted, reminiscent of the senile plaques described in the brains of patients with Alzheimer's disease.

EXAMPLE 3

EFFECT OF β-AMYLOID AND NGF ON MELANOCYTES

In neurons, the protein product of the proto-oncogene Bcl-2 delays the onset of apoptosis triggered by a variety of stimuli, while overexpression of a Bcl-2 associated protein (Bax) accelerates this cell death.

To investigate the mechanism of β-amyloid-mediated melanocyte death, Bax levels in melanocytes treated with 25 µM of 1–40 or 25–35 β-amyloid peptides was examined. Within 4 days of treatment, Bax was induced 3 fold in melanocytes stimulated either with the β-amyloid 1–40 or 25–35 fragments as compared to melanocytes treated with the 40–1 control fragment or an irrelevant HPLC purified protein of similar size.

Melanocytes were maintained as above. Four days after addition of 25 µM of β-amyloid fragments 1–40, 40–1 or 25–35; or 25 µM of HPLC-purified bovine corticotropin releasing factor (CRF) (Bachem Calif.) (MW 4.7 kD) as an additional negative control, cells were extracted in RIPA buffer (50 mM Tris-HCl [pH 8.0], 0.15 M NaCl, 0.5% sodium deoxycholate, 1% Triton™ X-100) in the presence of 1 µg/ml aprotinin and 75 µg/ml phenylmethylsulfonyl fluoride (PMSF), sonicated for 1–3 seconds and centrifuged. 40 µg of protein per lane were separated on 12% SDS/PAGE and blotted onto nitrocellulose paper (overnight, 25V). To verify equal loading a duplicate 13% SDS/PAGE was performed and stained with Coomasie Blue R250 stain. Blots were incubated with anti-Bax antibody (1:1000 dilution) (primary antibody), followed by horseradish peroxidase-conjugated goat anti-rabbit IgG (secondary antibody) (1:500 dilution) (Bio-Rad Laboratories, Hercules, Calif.). Bound antibodies were detected using enhanced chemiluminescence kit (Amersham Corp.). Autoradiograms were scanned into a Macintosh II is computer using the Ofto™ program (Light source Computer Images, Inc.). Scan analysis was performed with manual definition of bands using Scan Analysis™ 68000 program (Biosoft, Cambridge, UK).

β-amyloid peptides 1–40 and 25–35 increased Bax level as compared to the 40–1 peptide (270% and 160%, respectively).

EXAMPLE 4

EFFECT OF NGF ON P-AMYLOID INDUCED CELL DEATH

Nerve growth factor (NGF) has been reported to improve cognitive function and attenuate loss of cholinergic neurons in animal models and in clinical treatment trials for Alzheimer's disease (Seiger, A., et al., *Behave. Brain. Res.*, 57:255–261 (1993); Lapchak, P. A., *Exp. Neurol.*, 124:16–20 (1993); Olson, L., et al., *J. Neural. Transm. Park. Dis. Dement. Sect.*, 4:79–95 (1992)). Furthermore, it has been recently reported that NGF delays melanocyte apoptosis by upregulating the levels of Bcl-2 (Zhai, S., et al. *Exp. Cell. Res.* It was investigated whether NGF supplementation protects melanocytes from β-amyloid-induced cell death. Addition of NGF to β-amyloid-supplemented melanocytes enhanced cell yields within 3–5 days and greatly improved the morphology of surviving cells in most donors, although degree of protection was variable among donors. Preliminary data suggest that NGF supplementation decreases the β-amyloid-induced Bax upregulation and increases Bcl-2 levels in the cells suggesting that NGF interferes with β-amyloid-mediated signal transduction.

Melanocytes were maintained as above in hormone supplemented medium lacking hydrocortisone. Cells were supplemented with 25 µM of β-amyloid 1–40 in the presence of 50 ng/ml NGS or diluent.

Photographs of representative fields were obtained and the percent of the live cells (spread) was determined 48 hours after addition of β-amyloid and NFG or β-amyloid and diluent. In the presence of β-amyloid and diluent 77±8.5% appeared spread as compared to 96±1.4% in cultures supplemented in β-amyloid and NGF. In cultures not provided β-amyloid and diluent even the cells that were still spread on the dish surface were vacuolated and generally did not appear as healthy as cells in NGF supplemented cultures.

β-amyloid exposed melanocytes in the absence of NGF are dying, while in the presence of NGF the cells appear healthy and spread on the dish surface. At least 400 cells were counted in each condition.

EXAMPLE 5

β-AMYLOID BINDS THE p75 NERVE GROWTH FACTOR RECEPTOR

To determine if β-amyloid binds $p75^{NTR}$, $^{125}I$ labeled 1–40 β-amyloid peptide was added to permanently transfected cultured fibroblasts that overexpress $p75^{NTR}$ ($p75^{NTR}$-NIH 3T3 cells) (Dobrowsky, T. T., et al., Science, 265:1596 (1994) in the presence of disuccinimidyl suberate to cause cross linking of closely associated proteins. Cells were then immunoprecipitated with anti $p75^{NTR}$ antibodies or an irrelevant mouse IgG. Autoradiograms revealed a protein band of 75–80 kD in size only in lysates immunoprecipitated with anti $p75^{NTR}$ antibodies. Competition analysis of $^{125}I$ 1–40 β-amyloid in the presence of increasing concentrations of unlabeled NGF showed that 1–40 β-amyloid could be competed off by NGF. However, residual $^{125}I$ labeled 1–40 binding suggests that 1–40 1 β-amyloid may have an additional cell surface receptor, perhaps the recently identified serpin-enzyme complex receptor.

Results indicate that $p75^{NTR}$ is a receptor for β-amyloid, a peptide that is reported to be secreted into the medium of normal cells in high picomolar to low nanomolar concentrations. $p75^{NTR}$-NIH 3T3 cells were maintain in DMEM supplemented with 10% FBS in the presence of penicillin (45 ng/ml), streptomycin (68 ng/ml), and hygromycin B (17.5 ng/ml). At 80% confluence cells were lifted from the dish with EDTA and incubated in suspension with 5 uCi $^{125}I$ labeled β-amyloid 1–40 at 4° C. for 1 hour in DMEM. After incubation, 1 mM of disuccinimidyl suberate was added for 30 minutes. Following centrifugation cells were lysed with RIPA buffer (50 mM Tris HCl, pH 8.0, 0.15 M NaCl 0.5% sodium deoxycholate 4, 5 mM $MgC_2$, 1% Triton™ x-100, 1 mM phenylmethylsulfonylfluoride [PMSF], and 1 µg/ml aprotinin), sonicated for 1–3 seconds and immunoprecipitated with anti $p75^{NTR}$ antibodies (mouse monoclonal IgGl, Cedarlane Laboratories Ltd., Ontario, Canada) or mouse IgG as control for 16 hours at 4° C. in the presence of 15 ul of protein G plus protein A agarose and 1M NaCl adjusted to pH 8.0. After several washes with 20 mM Tris HCl, pH 8.0, 1M NaCl, 5 mM $MgCl_2$, 0.2% Triton™ X-100 and 1 mM PMSF, immunoprecipitates were separated over 8% PAGE and subjected to autoradiography. A band of appropriate molecular weight was present only in lysates immunoprecipitated with anti $p75^{NTR}$ antibodies and not lysates immunoprecipitated with irrelevant mouse IgG.

$p75^{NTR}$-NIH 3T3 cells were incubated for 2 hours at 4° C. in binding medium (DMEM, 10 mM hepes, 0.1 mg/ml cytochrome C, 0.01% Tween™ 80, 1 mg/ml BSA) with $^{125}I$ labeled β-amyloid 1–40 and increasing concentrations of NGF (0–100 ng/ml). After rinsing in PBS, cells were lysed in 1N NaOH and equal amounts of protein from cell lysates were subject to counting. A concentration dependent inhibition of $^{125}I$ labeled β-amyloid binding by NGF was observed with a maximum of 38% inhibition at NGF concentrations of 100 ng/ml and statistically comparable binding at 25 ng/ml.

EXAMPLE 6

Figure 1:
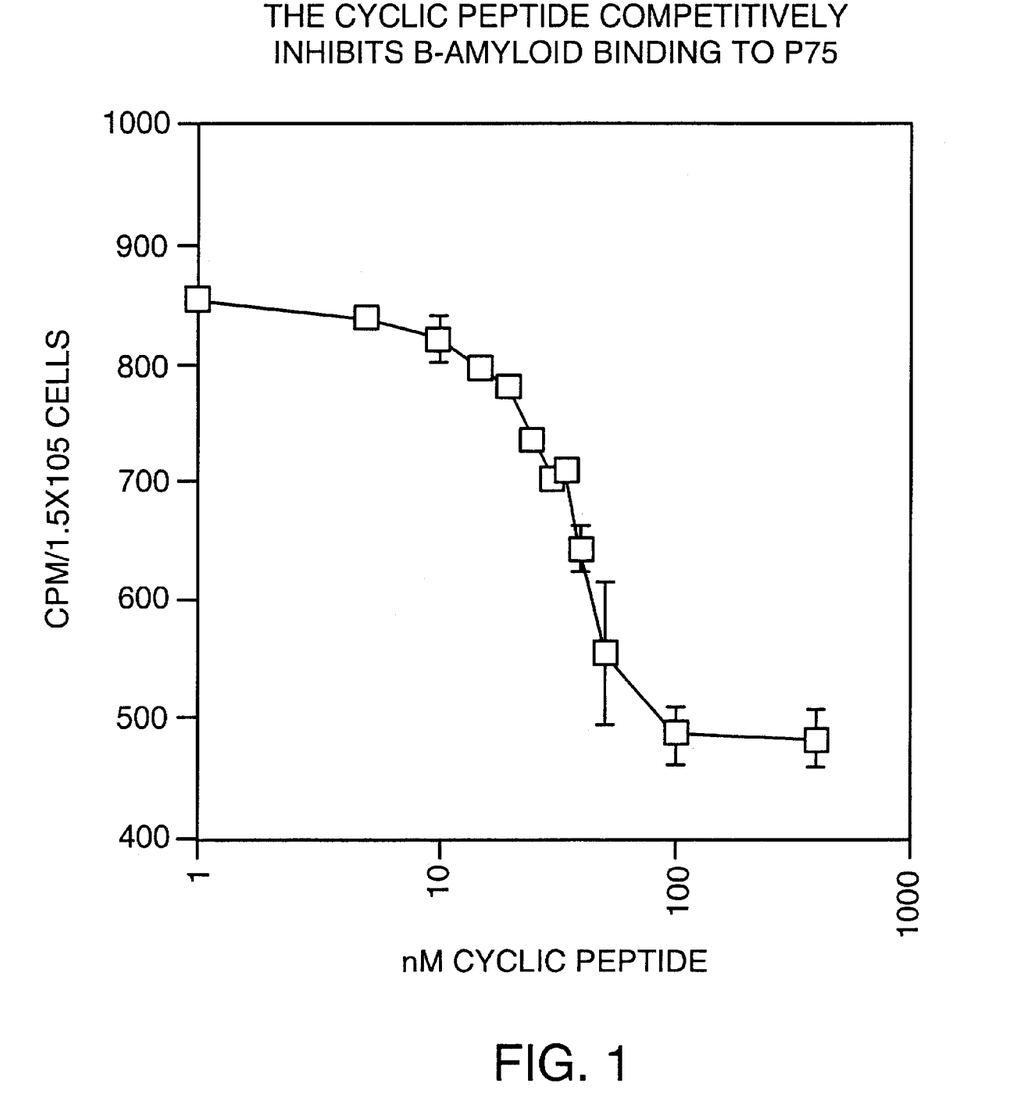
FIG. 1 is a graph depicting experimental results showing competition for binding to $p75^{NTR}$ by peptide versus β-amyloid.

CYCLIC PEPTIDE COMPETITIVELY INHIBITS β-AMYLOID BINDING TO $p75^{NTR}$ $p75^{NTR}$ 3T3 cells were incubated in suspension at 40° C. for 4 hours with 0.5 uCi $^{125}I$ labeled β-amyloid 1–40 and increasing concentrations (0–400 nM) of the cyclic peptide CVGSNKGAIC (SEQ ID NO: 4). Lysates from $1.5\times10^5$ cells were subjected to counting. As shown in FIG. 1, concentration dependent inhibition of $^{125}I$ labeled β-amyloid 1–40 binding by the cyclic peptide with 50% inhibition was observed at the expected 25 nM cyclic peptide concentration. This experiment demonstrates the cyclic peptide can compete with β-amyloid 1–40 for binding to the $p75^{NTR}$ receptor.

EXAMPLE 7

Figure 2:
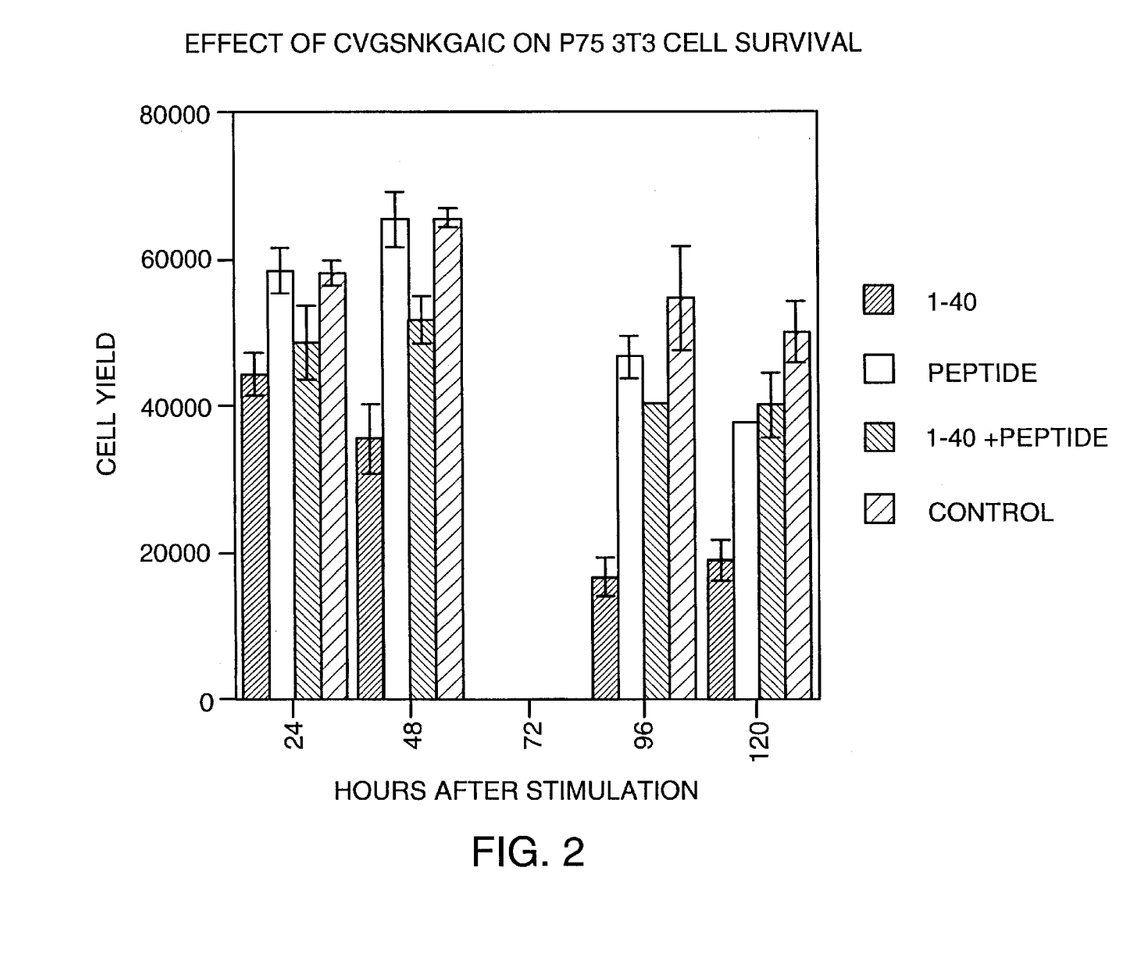
FIG. 2 is a graph depicting experimental results of the effect of peptide on a cell survival in the presence of β-amyloid.
Figure 3:
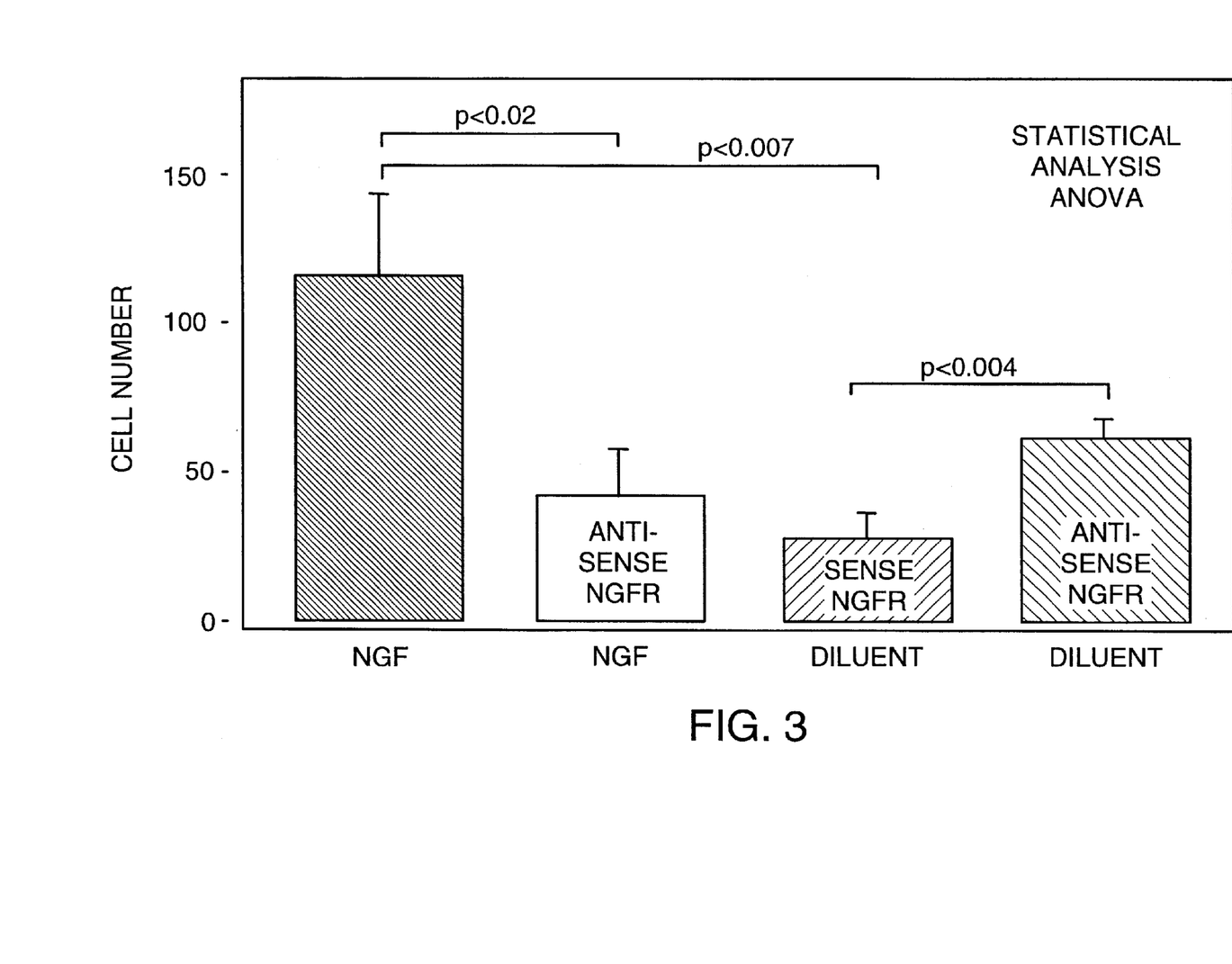
FIG. 3 is a graph showing the results of experiments showing melanocyte apoptosis and survival after treatment with anti $p75^{NTR}$ antisense nucleotide.

EFFECT OF PEPTIDE ON CELL SURVIVAL $p75^{NTR}$ 3T3 cells were maintained in serum free medium supplemented with 200 nM β-amyloid 1–40, 200 nM cyclic peptide CVGSNKGAIC, (SEQ ID NO: 4) 20 nM β-amyloid 1–40 and 200 nM cyclic peptide or diluent alone. Cell yields determined up to 120 hours after addition of β-amyloid show prominent decrease of cell yield in cultures maintained with 200 nM β-amyloid 1–40 as compared to all other cultures (see FIG. 2).

EXAMPLE 8

METHODS FOR TESTING THE LEVEL OF $p75^{NTR}$ mRNA AND PROTEIN IN SKIN SPECIMENS

Skin specimens will be obtained from early postmortem Alzheimer's disease patients and age matched controls. Specimens will be embedded and frozen in Tissue Tek II O.C.T. compound and processed for immunohistochemistry, in-situ Hybridization, and in-situ PCR.

IMMUNOHISTOCHEMISTRY

4–6 um thick vertical sections of skin will be incubated 1st with FITC conjugated mouse anti $p75^{NTR}$ monoclonal antibody as described (Yaar, M., et al., Lab. Invest., 58:175–162 (1988)). Then skin specimens will be incubated with Rhodamine conjugated anti TRP-1 antibody, a marker for cutaneous melanocytes. The intensity of anti-$p75^{NTR}$ antibody binding in melanocytes will reflect the level of $p75^{NTR}$. Quantification will be performed using a computer image analyzer (Allan, A. E., et al., J. Invest. Dermatol., 105:678–692 (1995)).

IN-SITU HYBRIDIZATION

Riboprobe Preparation:

The p75$^{NTR}$ cDNA will be cloned into a transcription vector pGEM-3Z containing both the T7 and PS6 polymerase promoter sites. Transcripts will be tested and the transcript that has been correct orientation that is complementary to p75$^{NTR}$ mRNA will be labeled with 35D-UTP (Allan, A. E., et al., J. Invest. Dermatol., 105:678–692 (1995)). 3 um sections will be cut, applied to glass slides and hybridized with the labeled probe. After extensive washes the slides will be dipped in liquid emulsion and placed at 4° C. for 10 days (Yaar, M., et al., Exp. Cell Res., 17:217–226 (1995)). At the end of the exposure period the slides will be developed and stained with hematoxylin and eosin. Slides will be viewed under light- and dark-field illumination and intensity of the labeling will be quantified using a computer image analyzer (Allan, A. E., et al., J. Invest. Dermatol., 105:678–692 (1995)).

IN-SITU PCR

In-situ PCR will be performed as described in Nuovo et al. (Nuovo, G. J., et al., Am. J. Pathol. 139:1239–1244 (1991)). Backward and forward primers spanning a 115 bp sequence of the coding region of p75$^{NTR}$ mRNA will be generated. Primers that span an intron will be selected to eliminate the possibility of amplifying genomic DNA. We will use reagents provided by the Gene Amp core kit from Perkin-Elmer and follow the instructions of the manufacturer Nuovo et al. (Nuovo, G. J., et al., Am. J. Pathol. 139:1239–1244 (1991), Khan, Z. M., et al., J. Invest Dermatol., 106:667–672 (1996). 45 cycles of PCT amplification will be performed. After hybridization, slides will be incubated with anti TRP-1 antibodies and a secondary goat anti mouse IgG. Color detection will be carried out using the substrates 4-nitroblue tetrazolium and 5-bromo-4-chloro-3-indolyl phosphate. Samples will be counter stained with hematoxylin and eosin and viewed under light field illumination (Khan, Z. M., et al., J. Invest Dermatol., 106:667–672 (1996)). The intensity of p75$^{NTR}$ mRNA labeling will be quantified using a computer image analyzer.

EXAMPLE 9

THE DUAL FUNCTION OF THE p75$^{NTR}$ IN MELANOCYTE APOPTOSIS AND SURVIVAL

Melanocytes were UV irradiated with 25 Mj/CM$^2$ and then supplemented either with 10 µM anti p75$^{NTR}$ anti sense phosphothioate oligonucleiotides (CTCCCACTCGTCAT TCGAC SEQ ID NO: 5) directed against the 3' end of the p75$^{NTR}$ coding region, or the same concentration of sense oligonucleotides as a negative control. Half the cultures were provided with 50 ng/ml NGF and; half the cultures were provided diluent alone.

Immunohistochemical analysis confirmed that p75$^{NTR}$ was not expressed in cells treated with anti-p75$^{NTR}$ antisense oligonucleotides, but was expressed in the sense treated cells. Within 24 hours after irradiation; the following was observed the following were observed:

1. Cells expressing p75$^{NTR}$ (supplemented with sense oligonucleotides) and trk A and supplemented with NGF appear healthy (A), establishing the protective effect of NGF on melanocyte survival in the presence of both receptors.
2. The majority of the cells expressing p75$^{NTR}$ (supplemented with sense oligonucleotides) and trk A and supplemented with diluent instead of NGF are dying as apparent by their rounded morphology (B).
3. Cells not expressing p75$^{NTR}$ (supplemented with antisense oligonucleotides) but expressing trk A and provided with 50 ηg/ml NGF (C) do not appear as healthy or numerous as cells expressing both receptors in the presence of NGF (A), establishing that the presence of both NGF receptors is required for optimal NGF effect.
4. Cells not expressing p75$^{NTR}$ (supplemented with antisense oligonucleotides) although they were not provided NGF (D) appear as healthy as cells provided NGF lacking p75$^{NTR}$ (C) establishing that p75NTR is required to induce melanocyte apoptosis.

EQUIVALENTS

While this invention has been particularly shown and described with references to preferred embodiments thereof, it will be understood by those skilled in the art that the various changes in form and details may be made therein without departing from the spirit and scope of the invention as defined by the appended claims.

---

What is claimed is:

1. A method of inhibiting β-amyloid binding to the p75 nerve growth factor receptor of a cell comprising contacting the cell with a polypeptide comprising the amino acid sequence lysine-glycine-alanine, wherein the polypeptide binds to the p75 nerve growth factor receptor, resulting in the inhibition of β-amyloid protein or β-amyloid peptide binding to the p75 nerve growth factor receptor.

2. The method of claim 1, wherein the polypeptide is selected from the group consisting of: SEQ ID NO.: 1; SEQ ID NO.: 3 and SEQ ID NO.: 4.

3. A method of inhibiting β-amyloid-mediated activation of the p75 nerve growth factor receptor of a cell comprising contacting the cell with a polypeptide comprising the amino acid sequence lysine-glycine-alanine, wherein the polypeptide binds to the p75 nerve growth factor receptor resulting in the inhibition of β-amyloid protein or β-amyloid peptide activation of the p75 nerve growth factor receptor.

4. The method of claim 3 wherein the polypeptide is selected from the group consisting of: SEQ ID NO.: 1; SEQ ID NO.: 3 and SEQ ID NO.: 4.

5. A method of inhibiting β-amyloid binding to the p75 nerve growth factor receptor of a cell comprising contacting the cell with a polypeptide comprising the amino acid sequence lysine-glycine-lysine, wherein the polypeptide is about 5 to about 10 amino acids in length and wherein the polypeptide binds to the p75 nerve growth factor receptor resulting in the inhibition of β-amyloid protein or β-amyloid peptide binding to the p75 nerve growth factor receptor.

6. The method of claim 5 wherein the polypeptide is derived from a sequence selected from the group consisting of: nerve growth factor, and a biologically active fragment of nerve growth factor.

7. The method of claim 5 wherein the polypeptide comprises SEQ ID NO.: 2.

8. A method of inhibiting β-amyloid-mediated activation of the p75 nerve growth factor receptor of a cell comprising contacting the cell with a polypeptide comprising the amino acid sequence lysine-glycine-lysine, wherein the polypeptide is about 5 to about 10 amino acids in length and wherein the substance binds to the p75 nerve growth factor receptor resulting in the inhibition of β-amyloid protein or β-amyloid peptide activation of the p75 nerve growth factor receptor.

9. The method of claim 8, wherein the polypeptide is derived from a sequence selected from the group consisting of: nerve growth factor and a biologically active fragment of nerve growth factor.

10. The method of claim 8 wherein the polypeptide comprises SEQ ID NO.: 2.

* * * * *

SEQUENCE LISTING

```
<160> NUMBER OF SEQ ID NOS: 5

<210> SEQ ID NO: 1
<211> LENGTH: 8
<212> TYPE: PRT
<213> ORGANISM: Homo sapiens

<400> SEQUENCE: 1

Val Gly Ser Asn Lys Gly Ala Ile
 1               5

<210> SEQ ID NO: 2
<211> LENGTH: 8
```

-continued

```
<212> TYPE: PRT
<213> ORGANISM: Homo sapiens

<400> SEQUENCE: 2

Thr Asp Ile Lys Gly Lys Glu Val
 1               5

<210> SEQ ID NO: 3
<211> LENGTH: 5
<212> TYPE: PRT
<213> ORGANISM: Artificial Sequence
<220> FEATURE:
<223> OTHER INFORMATION: Cyclic peptide

<400> SEQUENCE: 3

Cys Lys Gly Ala Cys
 1               5

<210> SEQ ID NO: 4
<211> LENGTH: 10
<212> TYPE: PRT
<213> ORGANISM: Artificial Sequence
<220> FEATURE:
<223> OTHER INFORMATION: Cyclic peptide

<400> SEQUENCE: 4

Cys Val Gly Ser Asn Lys Gly Ala Ile Cys
 1               5                  10

<210> SEQ ID NO: 5
<211> LENGTH: 19
<212> TYPE: DNA
<213> ORGANISM: Artificial Sequence
<220> FEATURE:
<223> OTHER INFORMATION: Oligonucleotide

<400> SEQUENCE: 5
ctcccactcg tcattcgac                                                  19
```